(12) United States Patent
Meadows et al.

(10) Patent No.: US 8,460,644 B2
(45) Date of Patent: Jun. 11, 2013

(54) SYNERGISTIC MIXED POLOXAMER SYSTEMS FOR THE SOLUBILISATION OF DRUGS

(75) Inventors: John Meadows, Newbridge (GB); Colum Martin Dwyer, Newbridge (GB)

(73) Assignee: IS Pharmaceuticals Limited, Chester (GB)

( * ) Notice: Subject to any disclaimer, the term of this patent is extended or adjusted under 35 U.S.C. 154(b) by 51 days.

(21) Appl. No.: 12/794,682

(22) Filed: Jun. 4, 2010

(65) Prior Publication Data

US 2010/0249240 A1    Sep. 30, 2010

Related U.S. Application Data

(63) Continuation of application No. 10/487,684, filed as application No. PCT/GB02/03910 on Aug. 23, 2002, now abandoned.

(30) Foreign Application Priority Data

Aug. 24, 2001 (GB) .................................. 0120701.8

(51) Int. Cl.
*A61K 8/81* (2006.01)
(52) U.S. Cl.
USPC ............... 424/70.15; 424/70.11; 424/70.19; 424/70.31; 514/937; 514/938; 514/941
(58) Field of Classification Search
None
See application file for complete search history.

(56) References Cited

U.S. PATENT DOCUMENTS

| | | | |
|---|---|---|---|
| 5,624,906 A | 4/1997 | Vermeer | |
| 5,817,321 A | 10/1998 | Alakhov et al. | |
| 6,153,193 A | 11/2000 | Kabanov et al. | |
| 6,623,765 B1 | 9/2003 | Dennis et al. | |
| 7,083,806 B2 * | 8/2006 | Rippon et al. | 424/484 |
| 2003/0138489 A1 | 7/2003 | Meadows et al. | |

FOREIGN PATENT DOCUMENTS

| | | |
|---|---|---|
| GB | 2 359 747 A | 9/2001 |
| WO | WO96/40056 | 12/1996 |
| WO | WO97/38675 | 10/1997 |
| WO | WO 00/78301 | 12/2000 |
| WO | WO01/64187 A2 | 9/2001 |

OTHER PUBLICATIONS

"Polymers in drug delivery," Uchegbu and Schatzlein ed., CRC press, pp. 111-125 (2006).
Attwood et al., "Poly(ethylene oxide) based copolymers: solubillsation capacity and gelation," Expert Opin. Drug Deliv. 4:533-546 (2007).
Chen-Chow et al., "In Vitro Release of Lidocaine From Pluronic F-127 Gels", International Journal of Pharmaceutics, vol. 8, 1981, pp. 89-99.
Florence and Atwood, "Physicochemical Principles of Pharmacy," MacMillan Press, pp. 243-250 (1998).
http://en.wikipedia.org/wiki/Lidocaine Jan. 25, 2007.
Kabanov et al., A new class of drug carriers: micelles of poly (oxyethylene)-poly (oxyproplene) block copolymers as microcontainers for drug targeting from blood in brain, Journal of Controlled Release 22 (1992) 141-158.
Mukerjee, Pure & Appl. Chem., vol 52, pp. 1317-1321. Pergamon Press Ltd. 1980.
Munshi et al., Ultrasound activated drup delivery from Pluronic P-105 micelles, Cancer Letters, 188 (1997) 13-19.
Rapoport, N., Stabilization and activation of Pluronic micelles for tumor targeted drug delivery, Colloids and Surfaces B-Biointerfaces (1999) 16, 1-4: 93-111.
Ruchatz et al., "The combination of Pluronic F127 and Pluronic F68—A new perspective for thermagelling drug delivery formulations." Proceedings of the Controlled Release Society (US), 25:896-897, 1998.
Scherlund et al., "Thermosetting microemulsions and mixed micellar solutions as drug delivery systems for periodontal anesthesia." International Journal of Pharmaceutics, 194: 103-116, 2000.

* cited by examiner

*Primary Examiner* — James Rogers
(74) *Attorney, Agent, or Firm* — Kilpatrick Townsend & Stockton LLP

(57) ABSTRACT

Drugs which are difficult to solubilize in water, and especially those which otherwise cause pain on injection, can be readily formulated and typically administered with substantially less pain when solubilized in synergistic, aqueous micellar preparations of poloxamers. Such preparations may also be prepared with less, or without, co-solvents.

8 Claims, 3 Drawing Sheets

SYNERGISTIC MIXED POLOXAMER SYSTEMS FOR THE SOLUBILISATION OF DRUGS

The present invention relates to novel pharmaceutical formulations, to their use and to their methods of manufacture.

In general, micellar solubilisation technologies are seldom capable of achieving levels of active materials in administration preparations that can be achieved by dissolution in direct solvent systems, whether they be oils, miscible solvent mixtures or the oil phase of an emulsion. Even micellar solubilisation systems using the effective poloxamer class of surfactants are rarely able to achieve sufficiently high levels of actives for administration purposes. Thus, actives which are poorly soluble in water must either be formulated in organic solvents, miscible cosolvent systems or as emulsions, if they are to be administered by injection.

Similar considerations apply to topical formulations, in that it is generally undesirable to use organic solvents, such as ethanol or propylene glycol, as they can be associated with side effects and other problems. For example, propylene glycol has been associated with such undesirable medical effects as superficial thrombophlebitis and intravasal haemolytic reactions, detected following the administration of parenteral formulations. For topical formulations, ethanol is generally associated with drying out of the skin, especially at higher concentrations, such as those that might be required to solubilise poorly water soluble actives.

Emulsions are inherently unstable, costly to produce, and often difficult to sterilise. These problems are very often further compounded by pain on injection for injectibles, often being associated with small amounts of the active present in the aqueous phase. For this reason, the use of water-miscible co-solvents is also undesirable, as these increase the solubility of the free drug in the continuous aqueous phase, thereby increasing any pain on injection associated therewith.

For injectibles, pain on injection is a significant issue when the active is dissolved in a suitable solvent, such as aqueous alcohol or aqueous glycol miscible cosolvent mixtures, as there will then be 100% of the active in the 'free' state at the point of injection. Any means of reducing this level of 'free' drug is, therefore, desirable as a potential means of reducing pain on injection. For example, formulation of diazepam into an emulsion form reduced the incidence of pain on injection to 0%, compared to formulation in a mixture of propylene glycol and water, which was associated with a 37% incidence of pain.

Poloxamers, which are also sold by BASF as Pluronics (US) and Lutrols (Europe), and by ICI as Synperonics, have been used for the solubilisation of drugs in the past. The drugs on which the poloxamers were tested either were difficult to administer by normal means, owing to their insolubility in water, or were thought likely to benefit from targeting, owing to their toxicity, for example.

Poloxamers, are polymeric surfactants generally suitable for use as therapeutic vehicles, and are block copolymers consisting of propylene oxide (PO) and ethylene oxide (EO) blocks—specifically, they are poly(a-oxyethylene-b-oxypropylene-a-oxyethylene) triblock copolymers. Their solubility in water is generally good, but the properties of the individual poloxamers vary substantially. The pharmaceutical acceptability of various poloxamers is well established, with P407 and P188, in particular, being approved for parenteral administration.

The nomenclature used for the "P" poloxamers, and generally herein, is such that the first two figures, when multiplied by 100, represent the average molecular weight of the PO block, whilst the last figure, when multiplied by 10, represents the ethylene oxide content (% w/w) of the poloxamer. Thus, for P407, the average molecular weight of the PO block is 4000 Daltons with a 70% w/w/ethylene oxide content.

The use of poloxamers to solubilise drugs is well known. In U.S. Pat. No. 6,153,193 (Supratek Pharma), for example, there is disclosed the use of poloxamers, together with a targeting molecule, for the delivery of selected drugs, including benzodiazepines. Combinations of poloxamers are disclosed, with the aim of manipulating micelle properties between room temperature and body temperature. No synergistic properties are apparent or disclosed for these combinations.

There have been problems with targeting and dispensing drugs using poloxamers. Munshi, et al. [Cancer Letters, 118 (1997), 13-19], found that it was not possible for the drug to act in a normal manner, unless ultrasound was used to disrupt the micelles. The use of ultrasound in surgical techniques is not only expensive, but undesirable.

Kabanov, et al. [Journal of Controlled Release, 22 (1992), 141-158], disclose a self-assembling supramacromolecular complex comprising drug, poloxamer and antibodies to try to target the drug contained within the thus-formed complex.

Rapoport, N. [Colloids and Surfaces B-Biointerfaces (1999) vol. 16, no. 1-4, 93-111], addresses Pluronic micelles as drug carriers. In particular, it notes that Pluronic micelles must be stabilised, and rules out the possibility of direct radical cross-linking of micelle cores, as this compromises drug loading capacity. A second route involves adding a small concentration of vegetable oil into dilute Pluronic solutions which, apparently, decreased micelle degradation on dilution. The preferred route was to polymerise a temperature-responsive LCST hydrogel in the core of the Pluronic micelles.

In co-pending application no. WO 01/64187, incorporated herein by reference, we disclose aqueous, micellar poloxamer preparations comprising Propofol which are stable at low concentrations, and which do not require the addition of co-solvents.

Thus, there remains a need for formulations of drugs that are poorly soluble in water.

Accordingly, in a first aspect, there is provided an aqueous preparation of a drug, characterised in that the drug is poorly soluble in water and is solubilised in the preparation by means of a synergistic mixture of poloxamers.

As used herein, a synergistic mixture of poloxamers is a combination of two or more poloxamers which, together with water, are capable of solubilising more of a drug than an equivalent amount of either or any one of the poloxamers of the combination under the same conditions.

By poorly soluble in water is meant that the drug is not sufficiently soluble in water to be therapeutically effective in what are considered to be convenient dosage sizes in the art. Many drugs suitable for use in the present invention cannot be sufficiently solubilised in water to be effective at all, and are only able to be presented in suitable quantity by solubilisation in organic solvents.

By aqueous preparations are meant preparations comprising at least 50% w/v water.

Preferred preparations are liquids, and are preferably suitable for injection. In an alternative embodiment, mobile gels or creams, such as those suitable for topical application, are preferred.

The poloxamers in the preparations of the present invention are preferably in micellar form.

Solutions of synergistic combinations of poloxamers, as described herein, have significant advantages over solutions of single poloxamers in that it is now possible to achieve target concentrations of actives, where this was either not previously possible, or only possible using unacceptably high concentrations of poloxamer. Although high levels of poloxamer are not necessarily a problem, per se, it is generally preferable to restrict amounts of non-aqueous components in injectibles. However, reducing the amount of poloxamer is particularly desirable from the point of view of formulation considerations. Poloxamers can have a substantial thickening effect on fluids, even at, or especially at, body temperature, so that reducing poloxamer concentrations may be desirable for injectibles where it is desired to permit standard hypodermic needles to be used, for example. In addition, high levels of poloxamers can be a significant problem in processing operations, such as filtering and filling, and reducing levels is also useful to reduce foam formation, which can happen at any production stage, as well as during mixing.

Synergistic mixed poloxamer systems are capable of solubilising more drug, often substantially more, than single poloxamer systems and, as such, result in greater partition coefficients of the active from water into the mixed poloxamer micelle, compared with the single poloxamer micelle. Thus, for a given poloxamer loading, synergistic mixtures can achieve a substantially higher loading of active than single systems. The greater partition coefficient also means that there will be a reduced amount of free drug present in the aqueous phase, which can be important where pain is associated with free drug in the aqueous phase. In such cases, the use of synergistic mixtures of poloxamers to solubilise such drugs for administration by injection is a particular advantage of the present invention.

It is a particular advantage of the present invention that, for injectibles associated with pain on injection, the pain can be reduced or eliminated where the drug is soluble in a synergistic mixture of poloxamers.

Examples of drugs that suffer from pain on injection, or that are difficult to formulate as injectibles, or in aqueous formulations in general, include: sedatives, such as diazepam; anaesthetic agents, such as etomidate; anti-schizophrenic agents, such as fluphenazine decanoate; and anti-fungal agents, such as miconazole.

It will also be appreciated that an advantage of the present invention lies in the absence of non-aqueous solvents, although it is not necessary to exclude their use altogether, especially for topical applications. In general, it is preferred to use a majority of water, especially deionised or sterile water, in any formulation, preferably a substantial majority, such as 85% or greater, preferably 90% or more of the non-poloxamer/drug component.

It is a particular advantage of the present invention that small amounts of pharmaceutically acceptable compounds can be used to solubilise problem drug in amounts greater than previously practicable. Thus, in preferred embodiments, water forms the major part of the formulation, by far.

It will be appreciated that the term 'drug', as used herein, refers to any therapeutic substance or compound, and especially those suitable for administration by injection. In particular, a drug used herein is soluble to a greater extent in a combination of poloxamers than in either or any of the poloxamers taken singly. The poloxamer combination is preferably of two or three poloxamers, and preferably with each poloxamer forming a minimum of 10% of total poloxamer. A preferred combination is of two poloxamers, especially where one is P407 and the other P188.

As used herein, the term "problem drug" relates to drugs suitable for use in the present invention, and are generally drugs that are associated with pain on injection, or which are not readily prepared in conventional formulations, especially aqueous formulations, or where conventional formulations of such drugs are not ideal for injection, or which are difficult to prepare, or which would otherwise benefit from being prepared as an aqueous formulation but where there is no suitable example in the art, although the present invention is not so limited, these being preferred examples.

Poloxamers are surfactants, and surfactants are amphiphilic substances. In other words, they comprise both hydrophilic and hydrophobic regions, and are commonly used to solubilise fatty substances in water. Above certain concentrations in water, surfactants tend to form micelles—agglomerations of surfactant molecules presenting their hydrophilic portions to water and internalising the hydrophobic portions. With increasing concentration, other structures may also be observed, but these tend to be somewhat complex. In the obverse, each surfactant has a minimum concentration in water below which micelles disperse (critical micelle concentration—CMC), and the aqueous surfactant preparation effectively becomes a solution of unimers with no structure.

Surfactant micelles are effectively envelopes and, in water, will have the more hydrophobic portion of the molecule generally forming the inside of the envelope. These micelles can readily interact with other substances and, if the substance is an oil, for example, then the substance can be entirely internalised within the micelle, or otherwise form an association, thereby effectively solubilising the substance in water.

Problem drugs may actually encourage micelle formation of the poloxamers in water, at temperatures and concentrations lower than would otherwise be expected, and often remain stable at infinite dilution. In those instances where micelle formation is catalysed, or even encouraged, it is believed that the drug is internalised within the micelle and serves to dramatically enhance the stability of the micelle.

Combinations of poloxamers are employed in the present invention. Surprisingly, it has been found that such combinations are synergistic, where the PO blocks have different sizes. Without being bound by theory, this is thought to be because of the formation of mixed micelles.

As noted above, poloxamers comprise PO units and EO units. The PO units are generally hydrophobic, and form the central portion of any micelle. In micelles with only one poloxamer, PO blocks align with each other, while EO blocks also align with each other on the outside, to form a thermodynamically stable system. In a mixed micelle, with poloxamers of differing PO length, when the PO blocks of different poloxamers align, either a "hole" is left in the micellar interior, or part of the EO block of the shorter poloxamer must align with the PO of the larger molecule. This is not thermodynamically stable and, with poloxamers that are substantially different, happens virtually not at all.

When drug is present, the formation of mixed micelles may often be encouraged, the drug compensating for the difference in PO block length, by occupying the space at the end of the shorter PO chain, thereby obviating the need for either a thermodynamically unfavourable association of EO and PO, or any tendency toward "holes", or both.

In practice, it will be appreciated that actual 'holes' would not be present within the micellar interior, as neighbouring PO blocks would adjust their configurations accordingly to compensate for the 'mismatch' in chain lengths. However, such configurational requirements would be entropically restrictive and, thus, thermodynamically unfavourable.

This ability of some problem drugs to stabilise mixed micelles has numerous advantages. First, it can stabilise the micelle to the extent that the micelle does not disaggregate even at infinite dilution, once formed, so that free drug is not released simply by the effects of dilution. Second, the effect can be sufficiently strong, that poloxamers which do not normally micellise, or are otherwise only sparingly soluble in water, readily form micelles in the presence of problem drug and another poloxamer, and vigorous mixing simply is not usually necessary. Third, the micelles may be thermodynamically stable, so that they will not disaggregate on storage and, if heated to disruption, will simply reform on cooling. Fourth, synergistically formed, mixed micelles effectively actively trap the drug, so that even less free problem drug is available in aqueous solution, thereby further reducing pain on injection in injectables, for example. Finally, in synergistic mixtures, less poloxamer is required to solubilise problem drug or, concomitantly, the same amount ensures that substantially all free problem drug is mopped up.

For example, the poloxamer known as P407 (also known as F127) has synergistic properties with P188 (also known as F68), which are generally greatest when the ratio of P407 to P188 is between about 7:3 and 3:7 by weight. It is generally preferred that the amount of P407 be at least equal to that of P188 by weight, but preferably greater.

The nature of the poloxamer is not essential to the present invention although, especially where the formulation is intended for administration to a human, it should be pharmaceutically acceptable. If the formulation is for dermal application, the requirements are not so severe, although it is preferred that the formulation be non-irritant.

Not only do drugs stabilise mixed poloxamer micelles but, for the majority of drugs, there is no requirement for the micelles to be targeted and that an extremely simple mix of drug, poloxamers and water is sufficient to make up a formulation of the invention. Furthermore, the mix may generally be autoclaved without problem, and may generally be prepared by simple roller mixing, as the preparations are thermodynamically stable, and form readily, depending on the drug.

Poloxamers are generally unreactive and non-responsive to any other additives to the system, such as BSA (Bovine Serum Albumin) or salt, such as sodium chloride. In addition, pH appears to have little, or no, effect. Thus, there is no problem with incorporating suitable substances to render the problem drug formulation suitable for injection, or colourants or emollients or other excipients in topical vehicles, for example, depending on the drug. In particular, it is preferred that the injectable formulations of the invention should be isotonic with the blood, so as not to cause any haemolysis, for example.

Individually preferred poloxamers are P188, P234, P237, P338 and P407. P407 and P188 are particularly preferred as they have been approved for medicinal purposes. P234 and P338 generally have better solubilisation abilities than P407, but neither has been approved. P237 also provides excellent uptake, but has yet to be approved.

Preferred problem drugs of the present invention are those drugs of the art which are associated with pain on injection, or which can only be inconveniently formulated, such as by the use of an organic solvent, such as alcohol. Given that preferred problem drugs are well known in the art, it will be appreciated that preferred concentrations of problem drug are also well known. Particularly preferred drugs and suitable administration concentrations therefor, are as exemplified above.

Even where single poloxamers are capable of providing preferred final concentrations, the use of synergistic combinations allows the use of less poloxamer as well as ensuring a greater partition of drug into the micelles.

As noted above, the PO blocks of synergistic poloxamers appear to be of different weights, although it is readily determined by one skilled in the art as to which combinations of poloxamers are synergistic. Even a combination of P108 and P188 is synergistic.

It appears that P401 has too little EO, and is not particularly useful in the present invention, as its lack of solubility in water is not significantly overcome by any drug.

In general, provided that there is a difference between two poloxamers, particularly between the PO portions, then a synergistic mixture will form. For example, a mix of P237 and P234, or a mix of P188 and P184, is not synergistic, but other mixes, such as: P407 with P338, P234, P237, P188 or P108; P338 with P234, P237, P188 or P108; P234 with P188 or P108; or P237 with P188 or P108 are all useful.

Any synergistic ratio is acceptable and useful. In general, a ratio of from about 1:1 to about 8:2 w/w is useful, with 1:1 to 7:3 being preferred.

It will be appreciated that the present invention further provides a method for the prophylaxis or treatment of the human or animal body by the administration of an effective amount of a preparation of the present invention thereto.

The hydrodynamic radii of micelles of poloxamers tend not to exceed about 10-20 nm, and are readily filterable through a 0.2 μm filter. Such filters are used commercially in order to sterilise formulations, and this is a further advantage of the present invention. A major drawback with emulsions, such as Diprivan, which is a preparation of the anaesthetic Propofol, is the lack of options for sterilisation of the formulation. In general, they cannot readily be filtered through a 0.2 μm filter, as the size of the emulsion particles is generally too great, and the emulsion is also too unstable to be autoclaved. By contrast, the formulations of the present invention are thermodynamically stable, so that they can be both filtered to sterility and/or autoclaved.

Autoclaving may be undesirable where filtering has achieved the required effect, and it should also be noted that autoclaving can have the effect of disrupting the micelles and the formulation in general, to the extent that re-mixing of the formulation may be required after autoclaving. This generally poses no particular problem because the formulations of the present invention are generally thermodynamically stable and, therefore, the constituents readily return to the favoured state of the formulation, although it can be inconvenient. It should also be noted that autoclaving may not be suitable if other constituents are present in the sterile formulation and which may be adversely affected by elevated temperatures.

Preparation of formulations of the present invention is generally straightforward. Although the constituents of the formulations can be added in any sequence, as desired, many preferred drugs are virtually insoluble in water, so that the generally commercially desirable method of mixing is to prepare a poloxamer solution in water, followed by the addition of problem drug, or dissolving the drug in the poloxamers prior to the addition of water. Solution of drug in poloxamers may be achieved with heating, if appropriate, where the poloxamers are solid at room temperature.

P407 is readily soluble in water, but heating of the water and the poloxamer, whilst mixing, can generally increase the speed of micelle formation. In addition, some poloxamers require increased temperatures in order to satisfactorily micellise in water. In general, concentrations of poloxamer of about 10% w/v are useful in the present invention, but concentrations of poloxamers, whether single or mixed, can be selected by those skilled in the art, and will generally be above 0.5% and below about 20%. More preferred concentrations are from 3 to 12%. Some poloxamers will begin to gel at higher concentrations, and any poloxamer concentration that gels at body temperature, especially when in association with a given problem drug, should be avoided for injection purposes. Preferred poloxamer mixes are those that enhance drug uptake and/or inhibit gelling, particularly at body temperature.

In one embodiment, the total poloxamer concentration is above 0.5% and below 20% w/w of the preparation, preferably between 2 and 12% w/v, more preferably between 3 and 8% w/v.

The amount of water in the formulation may be any that is desired, as discussed above, and preferably forms substantially all of the formulation except for the poloxamers and drug. In particular, it is preferred that water form between 75 and 95% of the formulation, more preferably 80 to 90% w/w.

Surprisingly, we have also found that it is readily possible to introduce a local anaesthetic into the formulations of the present invention, typically where the drug is not an anaesthetic itself. Thus, the present invention further provides a preparation as defined above, comprising, or further comprising, a local anaesthetic.

Thus, in instances where some pain on injection is still observed after formulating problem drug in a mixture of poloxamers and water, this can be reduced still further by the incorporation of a local anaesthetic into the preparation. Thus, pain is substantially reduced, and can often be reduced to nothing more than the pain associated with the injection apparatus itself. In the alternative, a topical formulation of lidocaine can be used to numb an area to be operated on locally, for example, or a topical preparation of carvacrol [2-methyl-5-(1-methylethyl)phenol] may be applied to sterilise an area of skin or a wound or other lesion.

Some preferred formulations of this aspect of the present invention have the advantage of mixing the active in a preparation together with lidocaine (2-diethylamino-2',6'-acetoxy-lidide), lignocaine, or other local anaesthetic, without having to prepare the injection immediately prior to use. This can be of particular advantage where other formulations of drug are unstable, or potentially unstable, in the presence of the local anaesthetic, for example.

The formulations of this aspect of the present invention may incorporate any suitable local anaesthetic. The anaesthetic may be chosen for its solubility profile, and it may be selected such that it is preferentially soluble in the aqueous phase. Ionically dissociable water soluble local anaesthetics suitable for parenteral use are preferred. In this respect, the hydrochloride forms are particularly preferred. A particularly preferred example is lignocaine hydrochloride, but other anaesthetics are also useful in the present invention, such as procaine hydrochloride, prilocaine hydrochloride, chloroprocaine hydrochloride, etidocaine hydrochloride, or mepivacaine hydrochloride. Suitable levels of local anaesthetic range from about 0.01% to 1% and, more preferably, between 0.05% w/v to 0.40% w/v. It will also be appreciated that anaesthetics should be chosen that are compatible with the active. Nevertheless, it will be appreciated that the freebase forms of drugs, such as lidocaine, are included in the present invention, a preparation incorporating lidocaine freebase being particularly preferred.

Drug can be added at any stage during preparation of a formulation, but it is currently preferred to add the drug to an aqueous solution of the poloxamer. Preferred problem drugs are naturally oils, and can simply be added to the poloxamer solution and incorporated into the solution in a roller mixing technique.

Solubilisation of many problem drugs into aqueous poloxamer solution occurs spontaneously upon gentle agitation. The fact that stable homogeneous systems can be prepared using such gentle agitation is indicative that the incorporation of problem drug into the aqueous system is through a mechanism of solubilisation into poloxamer micelles rather than through any emulsification mechanism. Micellar solubilisation, such as the incorporation of problem drug into P407 micelles, results in a thermodynamically stable system. It is energetically favourable for this type of system to form so only gentle agitation is required to facilitate adequate contact between the solubilising vehicle and the solubilised species. In contrast, most emulsions can be classed as kinetically stable systems. With such systems, sufficient energy must be applied to overcome a significant activation energy before they can form; this energy is usually applied through some form of high shear mixing. Similarly, once formed, there is a significant activation energy barrier to any de-emulsification process, although these systems may be broken, given sufficient time or the input of sufficient energy, e.g. centrifugation. Although kinetically stable systems can remain stable for a long time, thermodynamically stable systems, such as those of the present invention, have, technically, infinite long-term stability.

Where the drug is naturally a solid, this can first be solubilised either at higher temperatures in the presence of poloxamer, or in the presence of a suitable solvent, optionally at elevated temperature. The solvent may subsequently be removed from the final formulation by standard techniques, or allowed to remain. In the latter case, the present invention still allows for reduced amounts of solvent to be employed, by contrast with the art.

The formulations of the present invention need very few constituents. Drug, poloxamer mix and water is sufficient for a basic formulation, but it is greatly preferred that any injectable formulation is made up with saline, for example, in order to render the formulation isotonic, or iso-osmotic, with blood. In the preparations of the present invention, an appropriate level is about 0.40-0.60% w/v, in order to achieve an osmolality of about 300 mOsm, with a range of about 280-320 mOsm being generally desirable. Anything outside of this range may be used, but may possibly lead to perceptible pain.

Apart from the desirability of rendering injectable formulations isotonic with blood, it is generally preferred to minimise the number of other ingredients and to ensure that any formulation passed on to the patient is sterile. Given that the formulation can be sterilised after preparation, then this is not a particular problem.

Nevertheless, it may be desirable to incorporate sterilising agents, stabilising agents, and/or bacteriostats, for example. Prior art formulations have included sodium metabisulphite and EDTA (ethylene diamine tetraacetic acid), which may be incorporated in the formulations of the present invention, if desired. Propylene glycol may be used, for example, but this is not generally preferred. It will be appreciated that other additives may also be employed, such as antioxidants.

It will be readily appreciated by those skilled in the art how to administer formulations of the present invention to a human or animal. Amounts and times of administration will be generally indicated by the drug manufacturer. In particular, drugs used in the present invention are preferred to be administered by injection, although liquid formulations such as eye drops and ointments are also encompassed by the invention.

The formulations of the present invention can be provided in any suitable form and may be provided in any suitable containers appropriate to maintaining sterility. If necessary, the containers may be autoclaved immediately prior to use, although this is not preferred, and is not generally convenient.

The formulations of the present invention may also be provided as concentrates, although high concentrations of surfactants are generally not preferred and, in the case of certain poloxamers, can lead to gelation which is undesirable. Accordingly, it is generally preferred that the injectable formulations of the present invention be provided in a form suitable for direct injection. In such a capacity, any ampoule (for example) containing the formulation of the invention may, as appropriate, be used directly in a suitably adapted syringe to administer the formulation.

More generally, the ampoule, or other container, may be pierceable, or have a removable seal or cap, such that a syringe may be used to extract the solution, or the solution may be pourable directly into a syringe, or other apparatus for dosing the patient.

Gels and creams may be provided in tubs or tubes, and drops may be provided in dropper bottles, for example. Other suitable storage and dispensing means will be readily apparent to those skilled in the art.

The present invention will now be illustrated with respect to the following, non-limiting Examples in which, unless otherwise stated, all percentages are weight by volume and water used is sterile, deionised water. The Examples are illustrated with reference to the accompanying Figures, in which.

EXAMPLE 1

Preparation of Samples

Poloxamer Stock Solutions (500 ml):

10% w/v poloxamer solutions were prepared by adding 50 g of poloxamer, or poloxamer mix, to 350 ml of distilled water. This was then mixed using an overhead stirrer until completely dissolved. This solution was then made up to 500 ml with distilled water.

Problem Drug Formulations (20 ml):

0.1% w/v problem drug formulations were prepared by adding 0.02 g of problem drug to 20 ml of a stock solution, as prepared above. The solutions were then placed on a roller mixer to mix until all the problem drug had been solubilised (determined by visual evaluation), usually overnight, or for a sufficiently long period of time, sometimes up to 72 hours.

EXAMPLE 2

The maximum additive concentration (MAC) and degree of synergistic solubilisation was determined for a selection of water insoluble and sparingly soluble actives in aqueous P407+P188 mixtures.

For each active, the MAC was determined in the following aqueous poloxamer solutions:

10% w/w P407

7% w/w P407+3% w/w P188;

3% w/w P407+7% w/w P188

10% w/w P188

The actives that were examined are listed, along with their physical form and area of pharmacological activity, in Table 1.

TABLE 1

Actives investigated in P407 + P188 mixtures.

| Active | Physical form | Area of pharmacological activity |
|---|---|---|
| Fluphenazine Decanoate | Viscous oily liquid | Anti-schizophrenic |
| Fluphenazine Enanthate | Viscous oily liquid | Anti-schizophrenic |
| Lidocaine | Solid | Local anaesthetic |
| Carvacrol | Liquid | Antiseptic |

Figure 1:
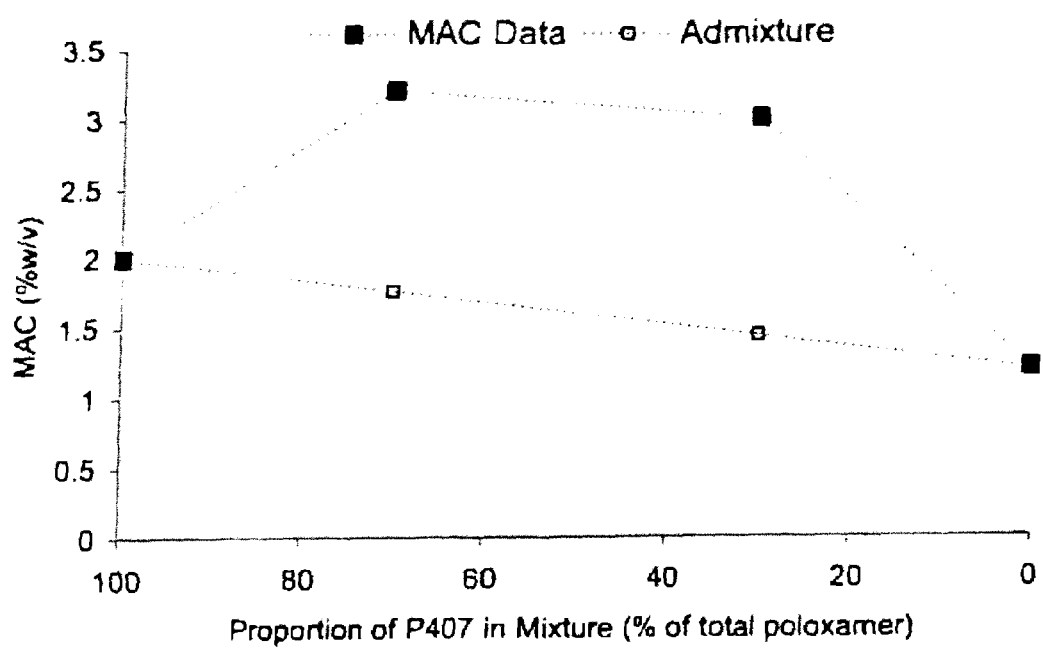
FIG. 1 shows maximum additive concentration (MAC) data for carvacrol.
Figure 2:
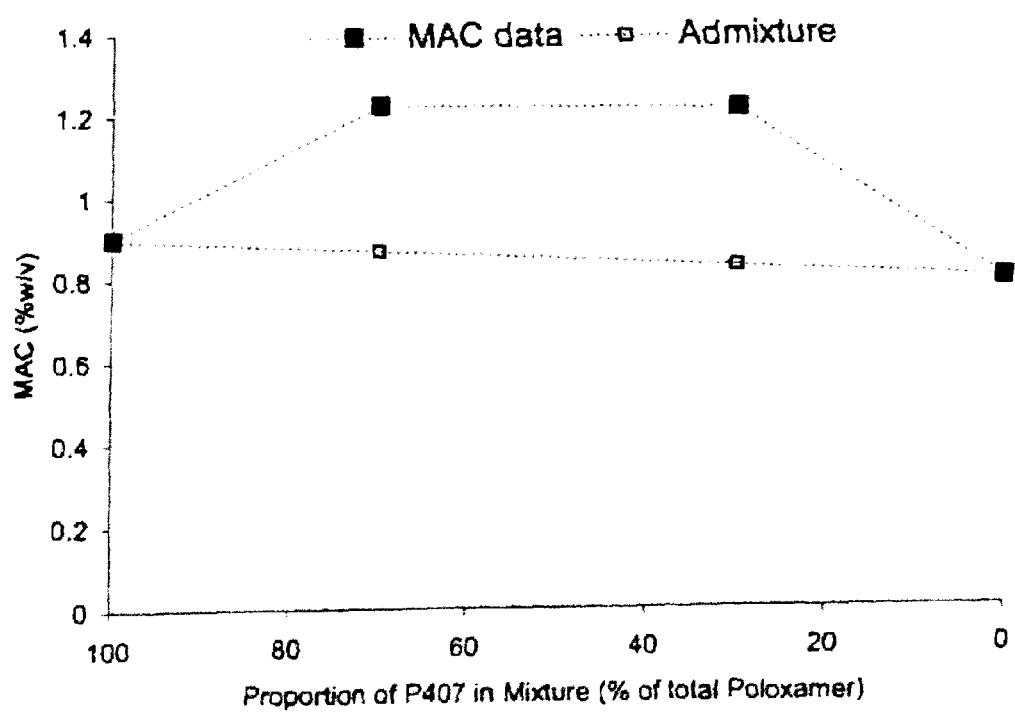
FIG. 2 shows MAC data for lidocaine.
Figure 3:
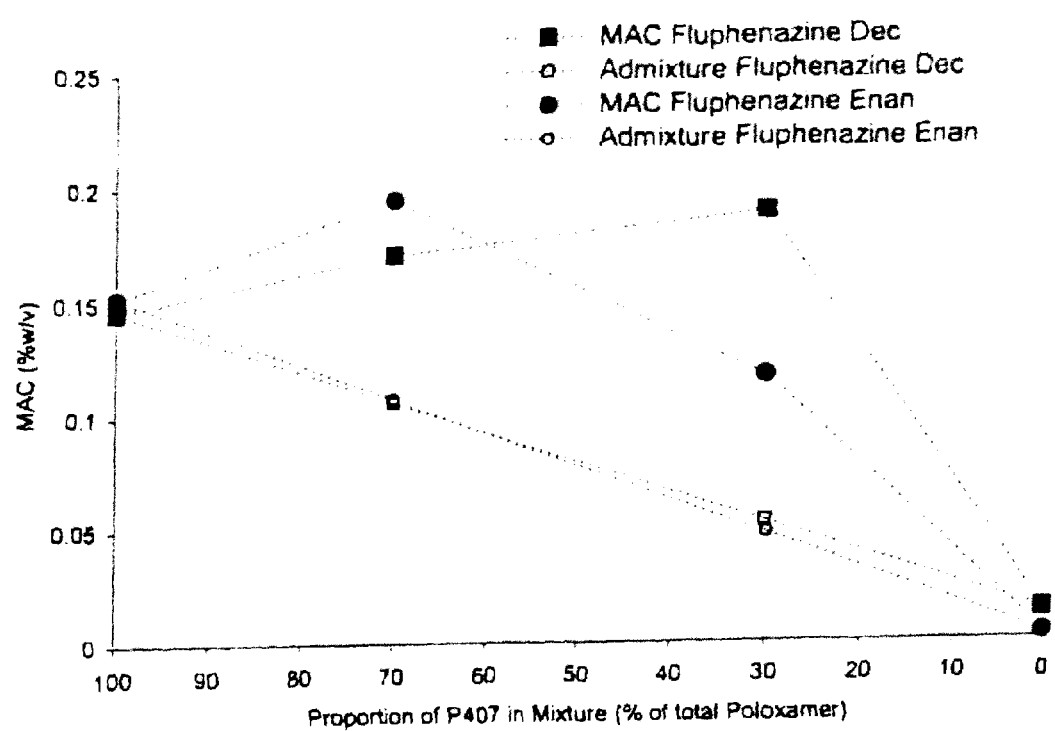
FIG. 3 shows MAC data for fluphenazine decanoate and fluphenazine enanthate.

As an aid to evaluating the level of synergistic solubilisation present within the system, the experimental data given in FIGS. 1-3 also includes the calculated MAC's of the systems that would be expected if the poloxamers comprising the mixture were solubilising independently and the overall MAC were simply the sum of the individual MAC's for the two components or admixture. It can be seen that the MAC's in each of the mixed systems are much greater than that which could be expected for the admixtures. The data are presented in Table 2.

In the accompanying Figures, data are shown for carvacrol in FIG. 1, lidocaine in FIG. 2, and fluphenazine decanoate (2-{4-[3-(2-trifluoromethyl-phenothiazin-10-yl)propyl]piperazin-1-yl}ethyl decanoate) and fluphenazine enanthate (2-{4-[3-(2-trifluoromethylphenothiazin-10-yl)propyl]piperazin-1-yl}ethyl heptanoate) in FIG. 3.

TABLE 2

Quantification of the level of synergistic solubilisation observed in mixtures of P407 + P188

| Active | 7% w/v P407 + 3% w/v P188 | 3% w/v P407 + 7% w/v P188 |
|---|---|---|
| Carvacrol | 1.8 | 2.1 |
| Lidocaine | 1.4 | 1.5 |
| Fluphenazine decanoate | 1.6 | 3.6 |
| Fluphenazine enanthate | 1.8 | 2.5 |

The figures represent the synergistic ratio, i.e. $MAC_{experimemtal}/MAC_{admixture}$

FORMULATION EXAMPLE 1

Fluphenazine Decanoate 100 ml of an antipsychotic formulation was prepared as follows:

9% w/v Poloxamer 407;

4% Poloxamer 188;

0.025% w/v Fluphenazine Decanoate;

0.4% w/v Sodium Chloride;

q.s. 100 ml Water for Injection.

Dilute sodium hydroxide solution or dilute hydrochloric acid solution (as required to render the solution pH 6.0-7.0)

All the components except fluphenazine decanoate were dissolved in the water. The fluphenazine decanoate was then added with gentle mixing until completely solubilised.

FORMULATION EXAMPLE 2

Fluphenazine Decanoate 100 ml of an antipsychotic formulation was prepared as follows:

3% w/v Poloxamer 407;
7% w/v Poloxamer 188;
0.025% w/v Fluphenazine Decanoate;
0.52% w/v Sodium Chloride;
q.s. 100 ml Water for injection
Dilute sodium hydroxide solution or dilute hydrochloric acid solution (as required to render the solution pH 6.0-7.0)
All the components except fluphenazine decanoate were dissolved in the water. The fluphenazine decanoate was then added with gentle mixing until completely solubilised.

FORMULATION EXAMPLE 3

Fluphenazine Decanoate 100 ml of an antipsychotic formulation was prepared as follows:
4% wry Poloxamer 407;
3% w/v Poloxamer 188;
0.025% w/v Fluphenazine Decanoate;
0.65% w/v Sodium Chloride;
q.s. 100 ml Water for injection
Dilute sodium hydroxide solution or dilute hydrochloric acid solution (as required to render the solution pH 6.0-7.0)
All the components except fluphenazine decanoate were dissolved in the water. The fluphenazine decanoate was then added with gentle mixing until completely solubilised.

FORMULATION EXAMPLE 4

Fluphenazine Decanoate 100 ml of an antipsychotic formulation was prepared as follows:
3% w/v Poloxamer 407;
7% w/v Poloxamer 188;
0.025% w/v Fluphenazine Decanoate;
0.1% w/v Lignocaine hydrochloride
0.52% w/v Sodium Chloride;
q.s. 100 ml Water for injection
Dilute sodium hydroxide solution or dilute hydrochloric acid solution (as required to render the solution pH 6.0-7.0)
All the components except fluphenazine decanoate were dissolved in the water. The fluphenazine decanoate was then added with gentle mixing until completely solubilised.

FORMULATION EXAMPLE 5

Lidocaine 100 ml of a local anaesthetic formulation was prepared as follows:
7% w/v Poloxamer 407;
3% w/v Poloxamer 188;
1.0% w/v Lidocaine base;
0.52% w/v Sodium Chloride;
q.s. 100 ml Water for injection
Dilute sodium hydroxide solution or dilute hydrochloric acid solution (as required to render the solution pH 6.0-7.0)
All the components except lidocaine base were dissolved in the water. The lidocaine base was then added with gentle mixing until completely solubilised.

FORMULATION EXAMPLE 6

Fluphenazine Enanthate 100 ml of an antipsychotic formulation was prepared as follows:
7% w/v Poloxamer 407;
3% w/v Poloxamer 188;
0.025% w/v Fluphenazine Enanthate;
0.52% w/v Sodium Chloride;
q.s. 100 ml Water for injection.
Dilute sodium hydroxide solution or dilute hydrochloric acid solution (as required to render the solution pH 6.0-7.0)
All the components except fluphenazine decanoate were dissolved in the water. The fluphenazine enanthate was then added with gentle mixing until completely solubilised.

FORMULATION EXAMPLE 7

Lidocaine 100 ml of a local anaesthetic formulation was prepared as follows:
3% w/v Poloxamer 407;
7% w/v Poloxamer 188;
1.0% w/v Lidocaine Base
0.52% w/v Sodium Chloride;
q.s. 100 ml Water for injection.
Dilute sodium hydroxide solution or dilute hydrochloric acid solution (as required to render the solution pH 6.0-7.0)
All the components except lidocaine base were dissolved in the water. The lidocaine base was then added with gentle mixing until completely solubilised.

FORMULATION EXAMPLE 8

Carvacro 100 ml of a topical antiseptic formulation was prepared as follows:
3% w/v Poloxamer 407;
7% w/v Poloxamer 188;
1.0% w/v Carvacrol
q.s. 100 ml water for injection.
Dilute sodium hydroxide solution or dilute hydrochloric acid solution (as required to render the solution pH 6.0-7.0)
All the components except carvacrol were dissolved in the water. The carvacrol was then added with gentle mixing until completely solubilised.

FORMULATION EXAMPLE 9

Carvacro 100 ml of a topical antiseptic formulation was prepared as follows:
4% w/v Poloxamer 407;
2% w/v Poloxamer 188;
1.0% w/v Carvacrol
q.s. 100 ml water for injection
Dilute sodium hydroxide solution or dilute hydrochloric acid solution (as required to render the solution pH 6.0-7.0)

All the components except carvacrol were dissolved in the water. The carvacrol was then added with gentle mixing until completely solubilised.

FORMULATION EXAMPLE 10

Carvacrol 100 ml of a topical antiseptic formulation was prepared as follows:
- 4% w/v Poloxamer 407;
- 2% w/v Poloxamer 188;
- 1.0% w/v Carvacrol
- 0.1% w/v Lignocaine hydrochloride
- q.s. 100 ml water for injection
- Dilute sodium hydroxide solution or dilute hydrochloric acid solution (as required to render the solution pH 6.0-7.0)

All the components except carvacrol were dissolved in the water. The carvacrol was then added with gentle mixing until completely solubilised.

The invention claimed is:

1. A method for making a homogeneous aqueous preparation consisting of preparing a synergistic mixture of two poloxamers in water, and adding lidocaine thereto;
  wherein the ratio of poloxamers is between 7:3 and 3:7 by weight, and
  wherein the poloxamers are selected from the group consisting of P188, P234, P237, P338 and P407.

2. The method according to claim 1, wherein said synergistic mixture of poloxamers comprises micelles.

3. The method according to claim 1, wherein the poloxamers are P407 and P188.

4. The method according to claim 1, wherein said poloxamer mixture is between 3% and 15% w/v of said preparation.

5. A method of making a homogeneous aqueous preparation consisting of mixing lidocaine with a synergistic mixture of two poloxamers and adding water thereto;
  wherein the ratio of poloxamers is between 7:3 and 3:7 by weight, and
  wherein the poloxamers are selected from the group consisting of P188, P234, P237, P138 and P407.

6. The method according to claim 5, wherein said synergistic mixture of poloxamers comprises micelles.

7. The method according to claim 5, wherein the poloxamers are P407 and P188.

8. The method according to claim 5, wherein said poloxamer mixture is between 3% and 15% w/v of said preparation.

* * * * *